(12) United States Patent
Chapuis et al.

(10) Patent No.: US 7,501,539 B2
(45) Date of Patent: Mar. 10, 2009

(54) PROCESS FOR THE PREPARATION OF ALKYLIDENECYCLOPENTANONE DERIVATIVES

(75) Inventors: Christian Chapuis, Mies (CH); Hans Wüest, Thun (CH)

(73) Assignee: Firmenich SA, Geneva (CH)

( * ) Notice: Subject to any disclaimer, the term of this patent is extended or adjusted under 35 U.S.C. 154(b) by 620 days.

(21) Appl. No.: 11/114,538

(22) Filed: Apr. 26, 2005

(65) Prior Publication Data

US 2005/0187299 A1    Aug. 25, 2005

Related U.S. Application Data

(63) Continuation of application No. PCT/IB03/04886, filed on Oct. 30, 2003.

(30) Foreign Application Priority Data

Nov. 11, 2002    (WO) ........................ PCT/IB02/04747

(51) Int. Cl.
    *C07C 61/20*    (2006.01)
(52) U.S. Cl. .................................... 562/504
(58) Field of Classification Search .................. 562/504
    See application file for complete search history.

(56) References Cited

OTHER PUBLICATIONS

Kusuda et al , Vinyl anion equivalents.Part IV. Efficient Synthesis of 2-(1-hydroxyalkyl)-2-cylopenten-1-ones, Bulletin of the chemical soceity of Japan , 1993 66(9), 2720-4, ( copy of abstract page).*
Abstract: XP002272417, Shicheng et al; "A Facile Method For Synthesis Of Methyl Djhydrojasmonate And Dihydroneojasmonate", Chemical Abstracts Service. retrieved from STN Database accession No. 107:5862.
Fazila Zulfiqar and Abdul Malik , XP002272416: "Facile Approach To Versatile Chiral Intermediates For Fused Cyclopentanoid Natural Products", Zeitschrift Fur Naturfurschung B. Chemical Sciences., vol. 56, No. 11, 2001, pp. 1227-1234, (2001).
R. Gastri and M. E. Gaied , XP002272414, "Imidazole-Catalysed Baylis-Hillman Reactions; A New Route To Allylic Alcohols From Aldehydes And Cyclic Enones", Tetrahedron Letters.,vol. 43, No. 43,, pp. 7835-7836, Elsevier Science Ltd., (2002).

* cited by examiner

*Primary Examiner*—Taylor Victor Oh
(74) *Attorney, Agent, or Firm*—Winston & Strawn LLP

(57) ABSTRACT

The present invention relates to the field of organic synthesis and more particularly to a new process for the preparation of a compound of formula (I), in the form of any one of its isomers or a mixture thereof,

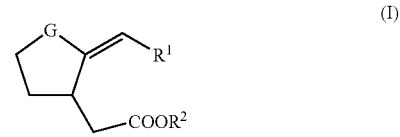

(I)

wherein, more preferably, G represents a C=O group, $R^1$ represents a butyl group and $R^2$ represents a methyl group.

The process of the invention involves an 2-(1-hydroxyalkyl)-cyclopent-2-en-1-one derivative, as starting material, which can be then converted into a compound of formula (I) by a process comprising a thermal rearrangement. The 2-alkylidene-3-oxo-cyclopentylacetate derivative and the 2-(1-hydroxyalkyl)-cyclopent-2-en-1-one derivative are also an object of the invention.

9 Claims, No Drawings

PROCESS FOR THE PREPARATION OF ALKYLIDENECYCLOPENTANONE DERIVATIVES

CROSS-REFERENCE TO RELATED APPLICATIONS

This application is a continuation of International application PCT/IB2003/004886 filed 30 Oct. 2003, the entire content of which is expressly incorporated herein by reference thereto.

TECHNICAL FIELD

The present invention relates to the field of organic synthesis and more particularly to a new process for the preparation of a 2-alkylidene-3-oxo-cyclopentylacetate derivative. Said process comprises the reaction of a 2-(1-hydroxyalkyl)-cyclopent-2-en-1-one derivative with a suitable orthoester or malonate to obtain an intermediate which undergoes a thermal rearrangement to give the desired final compound.

BACKGROUND

Cyclopentanone derivatives such as Hedione® (methyl 3-oxo-2-pentyl-1-cyclopentaneacetate; origin Firmenich S. A.), methyl 3-oxo-2-(2-pentenyl)-1-cyclopentaneacetate (methyl jasmonate) or methyl 3-oxo-2-pentyl-1-cyclopentene-1-acetate, are very important ingredients of the perfumery industry. Consequently, there is a need for new intermediates, and processes for their preparation, which can be advantageously employed in the synthesis of the above-mentioned perfuming ingredients.

In the literature there is no report, nor suggestion, of a process for the synthesis of a 2-alkylidene-3-oxo-cyclopentylacetate derivative, as defined below, involving the rearrangement of, a 2-(1-hydroxyalkyl)-cyclopent-2-en-1-one derivative as reported below.

Moreover, amongst the final compounds of the invention's process only methyl 3-oxo-2-pentylidene-cyclopentaneacetate is known in the prior art (S. Shicheng et al. in Youji Huaxue, 1986, 6, 453-6). However, said compound has been obtained by a process totally different from the one of the present invention. Furthermore, the 2-(1-hydroxyalkyl)-cyclopent-2-en-1-one derivative, as defined further below, have not been reported or suggested in the literature.

SUMMARY OF THE INVENTION

The invention relates to a process for the preparation of 2-alkylidene-3-oxo-cyclopentylacetate derivative. Said process comprises the reaction of a 2-(1 -hydroxyalkyl)-cyclopent-2-en-1-one derivative with a suitable orthoester or malonate to obtain an intermediate which undergoes a thermal rearrangement to give the desired final compound.

The 2-alkylidene-3-oxo-cyclopentylacetate derivative, as well as the 2-(1-hydroxyalkyl)-cyclopent-2-en-1-one derivative are also objects of the invention.

DESCRIPTION OF THE INVENTION

The present invention relates to a new process, aimed at the synthesis of a compound of formula (I), in the form of any one of its isomers or a mixture thereof,

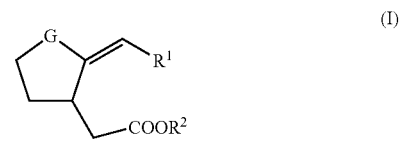

(I)

wherein G represents a C=O or C(OR)$_2$ group, R representing, taken separately, a C$_1$-C$_5$ alkyl group or, taken together, forming, together with the carbon and oxygen atoms of said G, a C$_3$-C$_7$ 1,3-dioxacycloalkane ring; and a) R$^1$ represents a n-butyl group or a CH$_2$X, CHO or CH$_{3-n}$Z$_n$ group, X standing for a halogen atom or a (3c-ethyl-bicyclo[2.2.1]hept-5-ene-2r-yl)methyl group;

n being 1 or 2 and Z standing for a C(OR')$_2$, OR$^3$ or SR$^3$ group; R' representing a group as defined previously as above R for G; and R$^3$ representing, taken separately, a C$_{1-7}$ benzyl, alkyl, cycloalkyl or oxacycloalkyl group or a C$_{1-7}$ acyl, sulfonyl or silyl group, or, taken together, forming, together with the carbon and oxygen or sulfur atom to which they are bonded, a C$_3$-C$_7$ 1,3-dioxacycloalkane or 1,3-dithiacycloalkane ring; and b) R$^2$ represents a linear or branched C$_1$ to C$_4$ alkyl group.

Said process comprises the conversion of a 2-(1-hydroxyalkyl)-cyclopent-2-en-1-one derivative of formula (II), in the form of any one of its isomers or a mixture thereof,

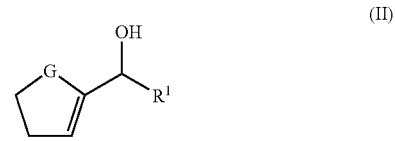

(II)

wherein G and R$^1$ have the meaning indicated in formula (I); into a compound of formula (I).

Preferred compounds of formula (I) or (II) are those wherein R$^1$ represents a n-butyl group or a CH$_2$X, CHO or CH$_{3-n}$Z$_n$ group, X standing for a halogen atom, n being 1 or 2 and Z standing for a OR$^3$ or SR$^3$ group, R and R$^3$ representing a group as defined above.

More preferably, in formula (I) or (II), G represents a CO group or a C$_{3-4}$ 1,3-dioxacycloalkane group, R$^1$ represents a n-butyl group, a C(OR)$_2$ group, R representing a group as defined above, a CH$_2$Cl or a CH$_2$Br group, or alternatively a CH$_2$OR$^3$ group, R$^3$ representing a C$_{1-7}$ benzyl, alkyl, cycloalkyl or oxacycloalkyl group or a C$_{1-7}$ acyl, sulfonyl or silyl group, and R$^2$ represents a methyl group. Even more preferably, G represents a CO group, R$^1$ represents a n-butyl group and R$^2$ represents a methyl group.

The conversion of the compound of formula (II) into a compound of formula (I), may be carried out by reacting the former with an orthoester, or a malonate, derivative to obtain an intermediate of formula (III) or (III'), respectively

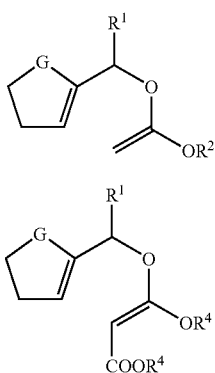

wherein G, $R^1$ and $R^2$ are as defined in formula (I) or (II), and $R^4$ represents a $R^2$ group or a $Si(R^5)_3$ group wherein $R^5$ is a $C_1$-$C_4$ alkyl group.

Said intermediate is subsequently thermally rearranged, e.g by a rearrangement of the Claisen type, and if necessary decarboxylated, to provide a compound of formula (I).

The isolation, or purification, of the intermediate (III) or (III'), prior to its conversion into (I), is not mandatory, so that the invention's process is carried out as a "one-pot" process.

Useful orthoesters or malonates are those of formula $CH_3C(OR^2)_3$ or $CH_2(COOR^4)_2$, respectively, $R^2$ and $R^4$ being defined above. Preferred orthoesters or malonates are those wherein $R^2$ represents a methyl group. The orthoesters are preferred over the malonates.

A specific example of the overall invention's process is given in following scheme:

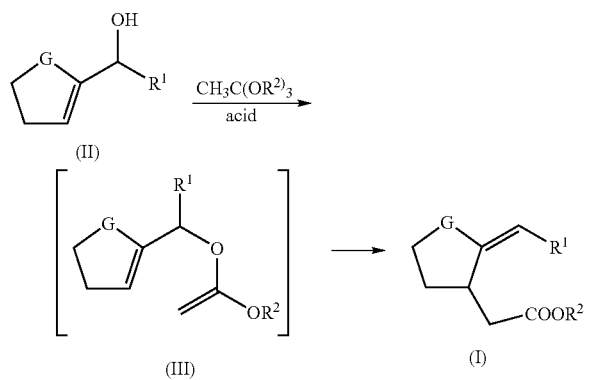

Scheme (1)

wherein G, $R^1$ and $R^2$ are as defined in formula (I) or (II).

The intermediate (III) or (III') are advantageously obtained by reacting together the compound of formula (II) with an orthoester or a malonate derivative in the presence of an acid, such as a $C_{1-10}$ carboxylic acid, optionally halogenated, or a $C_{1-10}$ sulfonic acid. Non limiting examples of such an acid are acetic, propionic, pivalic, trifluoroacetic, camphor sulfonic acid and p-TsOH (para toluenesulfonic acid). Said acid may be added in a catalytic amount, e.g. between 0.1 and 30 mol %, preferably between 5 and 20 mol %, with respect to the compound of formula (II).

The thermal rearrangement of the intermediate (III) or (III') is achieved by heating the reaction medium at a temperature comprised between 60° and 180° C., preferably between 90° and 120° C.

In the case where an orthoester derivative is used, it is understood that the intermediate (III) will provide directly a compound of formula (I) after the thermal rearrangement. However, in the case where there is used a malonate derivative, the rearrangement of the intermediate (III') will provide another malonate which will require a decarboxylation, more precisely a saponification followed by a decarboxylation and finally an esterification with an alcohol of formula $R^2OH$, wherein $R^2$ has the meaning indicated in formula (I), to provide a compound of formula (I).

All the transformations carried out in the invention process may be performed in the presence or absence of a solvent. Whenever a solvent is used, one can cite as non-limiting examples solvents such as the orthoester and malonate derivatives described hereinabove, aromatics (e.g. toluene or xylene) or hydrocarbons (e.g. decane or decaline).

Preferably, and in particular for the invention processes involving a compound (II) wherein $R^1$ represents a substituted methyl or methylene group, the thermal rearrangement is carried out under anhydrous conditions.

EXAMPLES

The invention will now be described in further detail by way of the following examples, wherein the abbreviations have the usual meaning in the art, the temperatures are indicated in degrees centigrade (° C.); the NMR spectral data were recorded with a 360 MHz machine in $CDCl_3$, the chemical displacement δ are indicated in ppm with respect to the TMS as standard, the coupling constant J are expressed in Hz and all the abbreviations have the usual meaning in the art.

Example 1

Synthesis of 2-(1-hydroxypentyl)-2-cyclopenten-1-one

A solution of cyclopentenone (1.23 g, 15 mmol), pentanal (1.94 g, 22.5 mmol), rac-1,1'-bi-2-naphthol (429 mg, 1.5 mmol) and tributyl phosphine (606 mg, 3 mmol) in dry THF (12 ml) was stirred at 20° C. under Argon for 3 hours. The solution was then passed through a short column of $SiO_2$ (cyclohexane/$Et_2O$ 6:4) to obtain the pure title compound in 92% yield.

IR: 3412, 2925, 2858, 1682, 1630, 1440. MS: 168 (M+, 0), 150(18), 135(10), 121(12), 111(100), 83(19), 55(16). $^1$H-NMR: 0.92 (t, J=7, 3H); 1.33 (m, 4H); 1.43 (s, 1OH); 1.68 (m, 2H); 2.45 (m, 2H); 2.60 (m, 2H); 4.46 (t, J=7, 1H); 7.49 (t, J=1.5, 1H). $^{13}$C-NMR: 14.0(q), 22.6(t), 26.6(t), 27.6(t), 35.3 (t), 35.6(t), 67.7(d), 148.0(s), 158.1(d), 210.4(s).

Synthesis of methyl 3-oxo-2-pentylidene-1-cyclopentaneacetate

A mixture of 2-(1-hydroxypentyl)-2-cyclopenten-1-one (720 mg, 4.2 mmol) and pivalic acid (100 mg, 0.98 mmol) in trimethylorthoacetate (5 ml, 39.3 mmol) was heated at 115° C. for 3 hours with distillation of MeOH. The concentrated reaction mixture was bulb-to-bulb distilled to afford the title compound in 88% yield and in the form of a 66:34 (Z)/(E) mixture.

Z isomer:

MS: 224(M+, 70), 167(18), 151(100), 133(23), 121(34), 109(54), 93(40), 79(46) $^1$H-NMR: 0.90 (t, J=7, 3H); 1.36 (m, 4H); 1.43 (m, 1H); 2.19 (m, 1H); 2.37 (m, 5H); 2.60 (dd, J=7,15, 1H); 2.70 (m, 1H); 3.70 (s, 3H); 5.90 (dt, J=2,7, 1H). $^{13}$C-NMR: 14.0(q), 22.4(t), 25.3(t), 27.3(t), 31.5(t), 38.2(t), 38.7(d), 39.4(t), 51.7(q), 137.8(s), 141.6(d), 172.5(s), 207.6(s)

E isomer:

MS: 224(M+, 70), 167(16), 151(100), 133(22), 121(29), 109(58), 93(36), 79(41), 67(22). $^1$H-NMR: 0.92 (t, J=7, 3H); 1.36 (m, 4H); 1.57 (m, 1H); 2.19 (m, 1H); 2.37 (m, 5H); 2.60 (dd, J=7,15, 1H); 2.71 (m, 1H); 3.70 (s, 3H); 6.59 (dt, J=2,7, 1H). $^{13}$C-NMR: 13.9(q), 22.5(t), 25.3(t), 29.0(t), 30.8(t), 35.0 (d), 35.8(t), 38.6(t), 51.8(q), 138.4(d), 139.8(s), 172.4(s), 206.4(s).

Example 2

Synthesis of Other Inventions Compounds a) General procedure for the preparation of the compounds of formula (II)

A solution of cyclopentenone (1.0 molar equivalents), the appropriate aldehyde (1.50 molar equivalents), 1,1'-bi-2-naphthol (0.1 molar equivalents) and nBu$_3$P (0.2 molar equivalents) in THF (800 ml/mol of cyclopentenone) is stirred at 20° C. under Argon for 3-15 hrs. The crude reaction mixture is passed through a short column of SiO$_2$ (chexane/ Et$_2$O 7:3) to separate the desired product from the starting aldehyde and nBu$_3$P as well as form 1,1'-bi-2-naphthol.

i) 2-(1-hydroxy-2,2-dimethoxyethyl)-2-cyclopenten-1-one

Obtained in 96% yield according to the general procedure and using glyoxal-1,1-dimethyl acetal (in the form of a 45% solution. in tBuOMe) as starting aldehyde.

IR: 3430, 2922, 2832, 1691, 1632, 1440, 1344, 1248, 1189, 1125, 1100, 972, 921, 789, 731. $^1$H-NMR: 1.5 (brs, 1 H); 2.45 (m, 2H); 2.67 (m, 2H); 3.43 (s, 3H); 3.46 (s, 3H); 4.5 (s, 2H); 7.65 (t, J=3, 1H). $^{13}$C-NMR: 27.0(t), 35.1(t), 55.3(q), 55.5(q), 67.6(d), 104.9(d), 147.7(s), 161.2(d), 209.2(s). MS: 186 (0, M$^{+\cdot}$), 155 (4), 123 (15), 75 (100), 47 (12).

ii) 2-[2-(Benzyloxy)-1-hydroxyethyl]-2-cyclopenten-1-one

Obtained in 65% yield according to the general procedure and using (benzyloxy) acetaldehyde as starting aldehyde.

IR: 3420, 2930, 2855, 1695, 1632, 1495, 1452, 1327, 1249, 1193, 1098, 1028, 1000, 900. $^1$H-NMR: 2.42 (m, 2H); 2.61 (m, 2H); 3.20 (brs, 1 H); 3.47 (dd, J=4, 7, 1H); 3.72 (dd, J=4, 7, 1H); 4.56, q, J=7, 2H); 4.67 (m, 1H); 7.28, (m, 5H); 7.62 (t, J=3, 1H). $^{13}$C-NMR: 26.8(t), 35.2(t), 66.9(d), 72.7(t), 73.3(t), 127.8(s), 127.8(2d), 128.5(2d), 137.8(s), 144.9(s), 160.0(d), 208.8(s). MS: 232 (0, M$^{+\cdot}$), 111 (66), 91 (100), 65 (18).

iii) 2- [2-(Ethyloxy)-1-hydroxyethyl]-2-cyclopenten-1-one

Obtained in 27% yield according to the general procedure and using 2-ethyloxy-acetaldehyde as starting aldehyde.

IR: 3429, 2972, 2865, 1739, 1690, 1632, 1439, 1347, 1248, 1111, 1063, 1030, 1000, 885, 789, 750. $^1$H-NMR: 1.2 (t, 3H); 2.3 (m, 1H); 2.45 (m, 2H); 2.62 (m, 2H); 3.4 (m, 1H); 3.55 (m, 2H); 3.7 (m, 1H); 4.65 (m, 1H); 7.65 (dt, J=2, 3, 1H). $^{13}$C-NMR: 15.1(q), 26.8(t), 35.2(t), 61.8(t), 66.7(d), 72.9(t), 145.1 (d), 159.9(s), 208.9(s). MS: 170 (1, M+.), 152 (23), 123 (15), 111 (100), 95 (20), 79 (18), 59 (19).

iv) 2-[(3-Ethylbicyclo[2.2.1]hept-5-en-2-yl)(hydroxy)methyl]-2-cyclopenten-1-one Obtained in 27% yield according to the general procedure and using 1.1 molar equivalent of a 6.5:1 mixture of cis-endo/cis-exo ethylbicyclo[2.2.1]hept-5-ene-2-carbaldehyde as starting aldehyde.

IR: 3500, 1703. $^1$H-NMR (main isomer): 0.92 (t, J=7, 3H); 1.2-1.6 (m, 2H); 1.86 (m, 1H); 2.18 (m, 1H); 2.31 (m, 2H); 2.4 (m, 2H); 2.6 (m, 2H); 2.95 (AB, 2H); 3.94 (d, J=7, 1H); 5.97 (m, 1H); 6.19 (m, 1H); 7.36 (t, J=3, 1H). $^{13}$C-NMR (main isomer): 13.3(q), 21.1(t), 33.3(d), 35.4(t), 38.1(t), 43.2(t), 44.1(d), 44.8(d), 45.9(d), 68.8(d), 134.5(d), 136.0(d), 147.5(s), 159.0(d), 210.1(s). MS: cis-endo stereoisomer 1 232 (1, M$^{+\cdot}$), 167 (8), 165 (6), 149 (100), 137 (17), 111 (19), 66 (45); cis-endo stereoisomer 2 232 (3, M$^{+\cdot}$), 167 (5), 165 (10), 149 (100), 137 (20), 111 (13), 66 (40); cis-exo stereoisomer 1 232 (2, M$^{+\cdot}$), 167 (5), 165 (7), 149 (100), 137 (17), 107 (18), 66 (51); cis-exo stereoisomer 2 232 (3, M$^{+\cdot}$), 167 (4), 165 (11), 149 (100), 137 (21), 111 (15), 66 (42).

b) General Procedure B for the Claisen Rearrangement

A mixture of a compound (II) (1.0 molar equivalents), trimethyl-orthoacetate (1770 ml/mol of compound (II)) and pivalic acid (0.17 molar equivalents) was heated at 120° C. for 3 hrs with distillation of MeOH. The reaction mixture was concentrated and bulb-to-bulb distilled to the corresponding compound (III) as E:Z mixtures.

i) Methyl [2-(2,2-dimethoxyethylidene)-3-oxocyclopentyl]acetate

Obtained in 96% yield according to the general procedure and using compound (II) described under a.i) as starting material. The reaction mixture was concentrated and bulb-to-bulb distilled (180° C./0.1 mbars) to afford title compound as a 3:2 E:Z mixture.

IR (major isomer): 2950, 2831, 1726, 1701, 1656, 1438, 1366, 1244, 1167, 1124, 1080, 989, 967, 891. (minor isomer): 2949, 2831, 1725, 1701, 1653, 1436, 1363, 1261, 1168, 1124, 1080, 965, 892. $^1$H-NMR (major isomer): 1.90 (m, 1H); 2.10 (m, 1H); 2.65 (m, 1H); 2.45 (m, 3H); 3.31 (s, 3H); 3.35 (s, 3H); 3.71 (s, 3H); 5.12 (d, J=7, 1H); 6.48 (dd, J=7, 3, 1H). (minor isomer): 1.90 (m, 1H); 2.10 (m, 1H); 2.65 (m, 1H); 2.35 (m, 3H); 3.40 (s, 3H); 3.43 (s, 3H); 3.71 (s, 3H); 5.75 (dd, J=7, 3, 1H); 5.90 (d, J=7, 1H). $^{13}$C-NMR (major isomer): 26.5(t), 35.2(d), 35.3(t), 38.6(t), 51.7(q), 52.1(q), 52.7(q), 99.7(d), 143.1(s), 161.7(d), 172.2(s), 206.5(s). (minor isomer): 27.0(t), 34.7(t), 38.0(t), 38.5(d), 49.7(q), 49.8(q), 50.0 (q), 97.2(d), 141.0(s), 161.1(d), 172.1(s), 206.7(s). MS(major isomer): 242 (20, M$^{+\cdot}$), 211 (80), 169 (100), 151 (96), 109 (59), 75 (73). (minor isomer): 242 (2, M$^{+\cdot}$), 211 (30), 195 (22), 169 (100), 151 (40), 109 (30).

ii) Methyl {2-[2-(Benzyloxy)ethylidene - 3-oxocyclopentyl}acetate

Obtained in 68% yield according to the general procedure and using compound (II) described under a.ii) as starting material.

IR: 2949, 1720, 1649, 1454, 1435, 1362, 1158, 1079, 1000, 926, 736, 697. $^1$H-NMR: 1.50 (m, 2H); 2.1-2.9 (m, 6H); 3.64 (s, 3H); 4.20 (d, J=7, 2H); 4.65 (AB, 2H); 6.68 (t, J=7, 1H); 7.32 (m, 5H). $^{13}$C-NMR: 27.0(t), 35.2(d), 37.7(t), 38.8(t), 51.7(q), 67.1(t), 71.4(t), 126.9(2d), 127.4(d), 128.4(2d), 132.8(d), 136.6(s), 150.1(s), 172.6(s), 206.1(s) MS: 288 (1, M$^{+\cdot}$), 197 (27), 165 (9), 91 (100), 65 (9).

iii) Methyl }2-[2-(Ethyloxy)ethylidene]-3-oxocyclopentyl}acetate

Obtained in 53% yield according to the general procedure and using compound (II) described under a.iii) as starting material. The product obtained is a mixture containing the E and Z isomer in a 1/1 ratio.

IR: 2952, 1720, 1697, 1650, 1436, 1406, 1375, 1156, 1002, 929, 890, 790. $^1$H-NMR: (E)-isomer: 1.2 (t, J=7, 3H); 1.5-2.7 (m, 7H); 3.5 (m, 2H); 3.7 (s, 3H); 3.75 (m, 2H); 6.62 (dt, J=2, 5.5, 1H); (Z)-isomer: 1.2 (t, J=7, 3H); 1.5-2.7 (m, 7H); 3.5 (m, 2H); 3.7 (s, 3H); 3.75 (m, 2H); 6.0 (dt, J=2, 5.5, 1H). MS: (E)-isomer: 226 (78, M$^{+\cdot}$), 197 (20), 170 (40), 153 (60), 125 (40), 111 (100), 98 (43), 83 (65); (Z)-isomer: 226 (62, M$^{+\cdot}$), 197 (40), 170 (40), 153 (100), 125 (97), 111 (80), 98 (40), 83 (50).

iv) Methyl[2-(3endo-ethylbicyclo[2.2.1]hept-5-en-2endo-yl]methylene]-3-oxocyclopentyl)acetate & methyl[2-(3exo-ethylbicyclo[2.2.1]hept-5-en-2exo-yl]methylene]-3-oxocyclopentyl)acetate Obtained in 55% crude yield according to the general procedure and using compound (II) described under a.iv) as starting material.

IR: 2955, 2930, 2870, 1736, 1702, 1629, 1608, 1458, 1435, 1407, 1377, 1260, 1230, 1192, 1150, 1093, 1051, 1002, 972, 892, 804, 791. $^1$H-NMR: 0.92 (t, J=7, 3H); 1.42 (sext, J=7, 2H); 1.55 (m, 2H); 1.69 (m, 2H); 1.88 (m, 1H); 2.05 (m, 1H); 2.22 (m, 2H); 2.35 (m, 2H); 2.45 (m, 1H); 2.50 (m, 2H); 2.62 (m, 1H); 3.28 (s, 3H); 6.09 (m, 2H); 7.32 (m, 1H). MS: 288 (4, M$^{+\cdot}$), 207(7), 117(8), 44(14), 32(27), 28(100).

v) Ethyl[2-(3endo-ethylbicyclo[2.2.1]hept-5-en-2endo-yl]methylene]-3-oxocyclopentyl)acetate & Ethyl[2-(3exo-ethylbicyclo[2.2.1]hept-5-en-2exo-yl]methylene]-3-oxocyclopentyl)acetate Using triethyl-orthoacetate instead of trimethyl-orthoacetate, and a bulb-to-bulb distilled (200° C./0.1 mbars) the title compound was obtained in 50% yield as a 1/2/3/4 mixture of 4 isomers ( cis-E/Z and endo/exo-isomers).

IR: 2955, 2930, 2870, 1735, 1700, 1630, 1610, 1460, 1435, 1405, 1380, 1260, 1230, 1190, 1150, 1095, 1050, 1000. $^1$H-NMR (main isomer): 0.80 (t, 3H); 0.85-1.25 (m, 3H); 1.26 (t, 3H); 1.30-3.5 (m, 12H); 6.55, (d, J=11, 1H); 4.18 (q, J=7, 2H); 6.05 (m, 1H); 6.25 (m, 1H). $^{13}$C-NMR (main isomer): 12.9(q), 14.3(q), 26.5(t), 34.6(d), 35.9(t), 38.4(t), 39.0(d), 42.9(d), 45.5(d), 46.7(t), 49.5(t), 49.9(d), 60.7(t), 134.9(d), 135.2(d), 136.8(s), 156.7(d), 172.1(s), 205(s). MS: cis-endo diastereoisomer 1, 302 (4, M$^{+\cdot}$), 237 (6), 236 (12), 207 (100), 149 (13), 117 (14), 91 (18); cis-endo diastereoisomer 2, 302 (20, M$^{+\cdot}$), 273 (17), 237 (11), 236 (14), 207 (100), 149 (19), 132 (36), 117 (56), 91 (42); cis-exo diastereoisomer 1, 302 (0, M$^{+\cdot}$), 237 (22), 236 (7), 207 (100), 149 (16), 91 (15); cis-exo diastereoisomer 2, 302 (10, M$^{+\cdot}$), 236 (10), 207 (100), 149 (19), 117 (22), 91 (28).

What is claimed is:

1. A process for the preparation of a compound of formula (I), in the form of any one of its isomers or a mixture thereof,

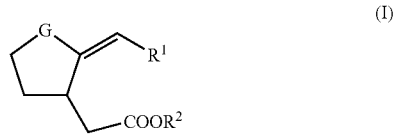

(I)

wherein G represents a C=O or C(OR)$_2$ group, R representing, taken separately, a C$_1$-C$_5$ alkyl group or, taken together, forming, together with the carbon and oxygen atoms of said G, a C$_3$-C$_7$ 1,3-dioxacycloalkane ring;

a) R$^1$ represents a n-butyl group or a CH$_2$X, CHO or CH$_{3-n}$Z$_n$ group, X standing for a halogen atom or a (3c-ethylbicyclo[2.2.1]hept-5-ene-2r-yl)methyl group;

n being 1 or 2 and Z standing for a C(OR)$_2$, OR$^3$ or SR$^3$ group;

R' representing a C$_1$-C$_5$ alkyl group alone or, when Z is C(OR')$_2$ or OR$^3$, forming, together with the carbon and oxygen atoms of said Z, a C$_3$-C$_7$ 1,3-dioxacycloalkane ring; and R$^3$ representing, taken separately, a C$_{1-7}$ benzyl, alkyl, cycloalkyl or oxacycloalkyl group or a C$_{1-7}$ acyl, sulfonyl or silyl group, or, taken together, forming, together with the carbon and oxygen or sulfur atom to which they are bonded, a C$_3$-C$_7$ 1,3-dioxacycloalkane or 1,3-dithiacycloalkane ring; and b) R$^2$ represents a linear or branched C$_1$ to C$_4$ alkyl group;
said process comprising:

(1) reacting a compound of formula (II),

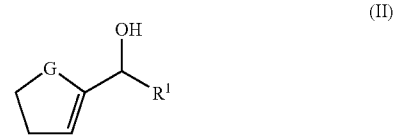

(II)

with an orthoester or a malonate compound of formula CH$_3$C(OR$^2$)$_3$ or CH$_2$(COOR$^4$)$_2$, respectively, and with an acid of a C$_{1-10}$ carboxylic acid, optionally halogenated, or a C$_{1-10}$ sulfonic acid to obtain a reaction mixture that includes an intermediate of formula (III) or (III'), respectively,

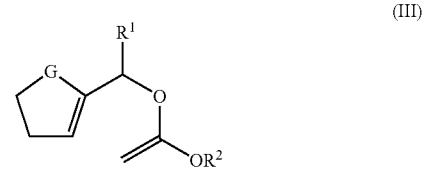

(III)

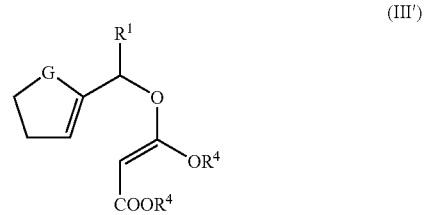

(III')

wherein R$^4$ represents an R$^2$ group or a Si(R$^5$)$_3$ group and R$^5$ is a C$_1$-C$_4$ alkyl group, and (2) heating the reaction mixture at a temperature range between 60° C. and 180° C. to thermally rearrange the intermediate of formula (III) or (III') to obtain the compound of formula (1); and optionally, if the malonate compound is used in step (1), the thermal rearranging of the intermediate of formula (III') is obtained by saponification, followed by decarboxylation and esterification with an alcohol of a formula R$^2$OH.

2. The process according to claim 1, wherein the compound of formula (II) is reacted with an orthoester of formula CH$_3$C(OR$^2$)$_3$.

3. The process according to claim 1, wherein R' represents a n-butyl group or a CH$_2$X, CHO or CH$_{3-n}$Z$_n$ group, X standing for a halogen atom, n being 1 or 2 and Z standing for a OR$^3$ or SR$^3$ group.

4. A process according to claim 3, wherein G represents a CO group or a C$_{3-4}$ 1,3-dioxacycloalkane group, R$^1$ represents a n-butyl group, a C(OR)$_2$ group, a CH$_2$Cl or a CH$_2$Br group, or a CH$_2$OR$^3$ group, with R$^3$ representing a C$_{1-7}$ benzyl, alkyl, Cycloalkyl or oxacycloalkyl group or a $C_{1-7}$ acyl, sulfonyl or silyl group, and $R^2$ representing a methyl group.

5. A process according to claim 4, wherein G represents a CO group, $R^1$ represents a n-butyl group and $R^2$ represents a methyl group.

6. A compound of formula

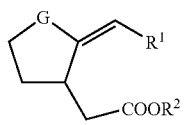

(I)

in the form of any one of its isomers or a mixture thereof, wherein G, $R^1$ and $R^2$ are as defined in claim 1; provided that methyl 3-oxo-2-pentylidene-cyclopentaneacetate is excluded.

7. A compound according to claim 6, wherein $R^1$ represents a n-butyl group or a $CH_2X$, CHO or $CH_{3-n}Z_n$ group, X standing for a halogen atom, n being 1 or 2 and Z standing for a $OR^3$ or $SR^3$ group.

8. A compound according to claim 6, wherein G represents a CO group or a $C_{3-4}$ 1,3-dioxacycloalkane group, $R^1$ represents a n-butyl group, a $C(OR)_2$ group, a $CH_2Cl$ or a $CH_2Br$ group, or alternatively a $CH_2OR^3$ group, $R^3$ representing a $C_{1-7}$ benzyl, alkyl, cycloalkyl or oxacycloalkyl group or a $C_{1-7}$ acyl, sulfonyl or silyl group, and $R^2$ represents a methyl group.

9. A compound according to claim 6, wherein G represents a CO group, $R^1$ represents a n-butyl group and $R^2$ represents a methyl group.

* * * * *

UNITED STATES PATENT AND TRADEMARK OFFICE
CERTIFICATE OF CORRECTION

PATENT NO.         : 7,501,539 B2                                          Page 1 of 1
APPLICATION NO.    : 11/114538
DATED              : March 10, 2009
INVENTOR(S)        : Chapuis et al.

It is certified that error appears in the above-identified patent and that said Letters Patent is hereby corrected as shown below:

<u>Column 8</u>:
Line 64, (claim 4, line 1), before "process", delete "A" and insert -- The --.

<u>Column 9</u>:
Line 3, (claim 5, line 1), before "process", delete "A" and insert -- The --.

Signed and Sealed this

Twelfth Day of May, 2009

JOHN DOLL
*Acting Director of the United States Patent and Trademark Office*